(12) United States Patent  (10) Patent No.: US 7,879,452 B2
Muslet  (45) Date of Patent: Feb. 1, 2011

(54) ELASTOMERIC FILMS WITH BRITTLE NONBLOCKING SKINS

(75) Inventor: Iyad Muslet, Mason, OH (US)

(73) Assignee: Clopay Plastic Products Company, Inc., Mason, OH (US)

( * ) Notice: Subject to any disclaimer, the term of this patent is extended or adjusted under 35 U.S.C. 154(b) by 0 days.

(21) Appl. No.: 11/433,253

(22) Filed: May 12, 2006

(65) Prior Publication Data

US 2006/0257666 A1   Nov. 16, 2006

Related U.S. Application Data

(60) Provisional application No. 60/680,168, filed on May 12, 2005.

(51) Int. Cl.
| | |
|---|---|
| B32B 27/36 | (2006.01) |
| B32B 27/40 | (2006.01) |
| B32B 27/06 | (2006.01) |
| B32B 27/04 | (2006.01) |
| B32B 27/00 | (2006.01) |
| B32B 27/08 | (2006.01) |
| B32B 29/00 | (2006.01) |

(52) U.S. Cl. ............... 428/500; 428/412; 428/475.8; 428/483; 428/492; 428/515; 428/537.5

(58) Field of Classification Search .................. None
See application file for complete search history.

(56) References Cited

U.S. PATENT DOCUMENTS

| | | | |
|---|---|---|---|
| 4,058,645 A | 11/1977 | Steiner | |
| 4,500,585 A * | 2/1985 | Erickson | ............. 428/152 |
| 4,880,682 A | 11/1989 | Hazelton et al. | |
| 4,952,451 A | 8/1990 | Mueller | |
| 5,057,097 A | 10/1991 | Gesp | |
| 5,112,674 A | 5/1992 | German et al. | |
| 5,127,977 A | 7/1992 | Eaton et al. | |
| 5,156,789 A | 10/1992 | Amaral et al. | |
| 5,344,691 A | 9/1994 | Hanschen et al. | |
| 5,354,597 A * | 10/1994 | Capik et al. | ............. 428/152 |
| 5,376,430 A | 12/1994 | Swenson et al. | |
| 5,422,178 A | 6/1995 | Swenson et al. | |
| 5,468,428 A | 11/1995 | Hanschen et al. | |
| 5,501,679 A | 3/1996 | Krueger et al. | |
| 5,620,780 A | 4/1997 | Krueger et al. | |
| 5,691,034 A | 11/1997 | Krueger et al. | |
| 5,709,953 A | 1/1998 | Goto et al. | |
| 5,800,903 A | 9/1998 | Wood et al. | |
| 5,807,368 A | 9/1998 | Helmer | |
| 5,885,908 A | 3/1999 | Jaeger et al. | |
| 5,888,640 A | 3/1999 | Marotta et al. | |
| 5,955,187 A | 9/1999 | McCormack et al. | |
| 6,221,483 B1 | 4/2001 | Hilston et al. | |
| 6,245,271 B1 | 6/2001 | Jacobs et al. | |
| 6,303,208 B1 | 10/2001 | Pelkie | |
| 6,322,883 B1 | 11/2001 | Williams | |
| 6,410,129 B2 | 6/2002 | Zhang et al. | |
| 6,410,645 B1 | 6/2002 | Pathak et al. | |
| 6,436,529 B1 | 8/2002 | Deeb et al. | |
| 6,472,045 B1 | 10/2002 | Morman et al. | |
| 6,475,600 B1 | 11/2002 | Morman et al. | |
| 6,495,266 B1 | 12/2002 | Migliorini | |
| 6,617,016 B2 | 9/2003 | Zhang et al. | |
| 6,638,636 B2 | 10/2003 | Tucker | |
| 7,041,367 B2 * | 5/2006 | Janssen et al. | ............. 428/341 |
| 2002/0187304 A1 | 12/2002 | McCormack et al. | |
| 2004/0247910 A1 | 12/2004 | Janssen et al. | |

FOREIGN PATENT DOCUMENTS

| | | |
|---|---|---|
| CN | 1384785 A | 12/2002 |
| WO | 01/15898 A1 | 3/2001 |
| WO | 03020513 | 3/2003 |

OTHER PUBLICATIONS

Chinese Patent Office, Chinese Office Action in corresponding CN Application No. 200680016038.1 dated May 22, 2009, 15 pages.
Chinese Patent Office, Chinese Office Action in counterpart CN Patent Application No. 200680016038.1 dated Dec. 4, 2009, 15 pp.
Examination Report received in corresponding AU Patent Application Serial No. 2006247348 dated Mar. 15, 2010, 4 pages.
Clarke Modet & Co., correspondence from Chilean associate reporting Office Action received in corresponding CL Patent Application Serial No. 1134-2006 dated Sep. 8, 2008, 5 pages.
Clarke Modet & Co., correspondence from Chilean associate reporting Office Action received in corresponding CL Patent Application Serial No. 1134-2006 dated Aug. 24, 2009, 3 pages.

(Continued)

*Primary Examiner*—Sheeba Ahmed
(74) *Attorney, Agent, or Firm*—Wood, Herron & Evans, LLP

(57) ABSTRACT

A nonblocking multilayer elastomeric-film comprises a first brittle polymer film layer bonded to a second elastomeric polymer film layer. The multilayer film is activatable to fracture the first brittle polymer layer and to render the multilayer film elastomeric.

41 Claims, 8 Drawing Sheets

OTHER PUBLICATIONS

Clarke Modet & Co., correspondence from Chilean associate reporting Office Action received in corresponding CL Patent Application Serial No. 1134-2006 dated Aug. 26, 2010, 3 pages.

Gorodissky & Partners, correspondence from Russian associate reporting Office Action received in corresponding RU Patent Application Serial No. 2007146144 dated May 19, 2010, 7 pages.

Patrick Mirandah Co., correspondence from Malaysian associate reporting Office Action received in corresponding MY Patent Application Serial No. PI20062224 dated Jun. 28, 2009, 5 pages.

International Searching Authority, Search Report and Written Opinion received in PCT Application Serial No. PCT/US2006/018903 dated Oct. 6, 2006, 10 pages.

* cited by examiner

Fig. 1-a
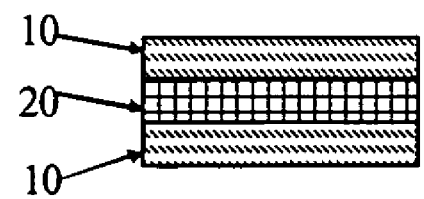
Fig. 1-b
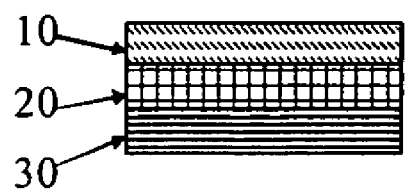
Fig. 1-c
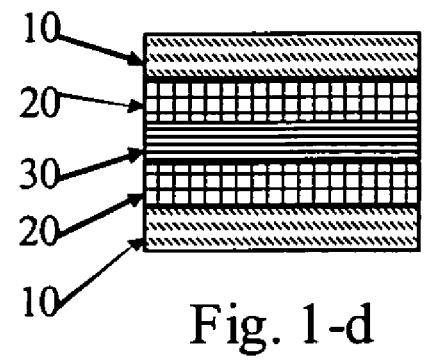
Fig. 1-d

At 20X magnification

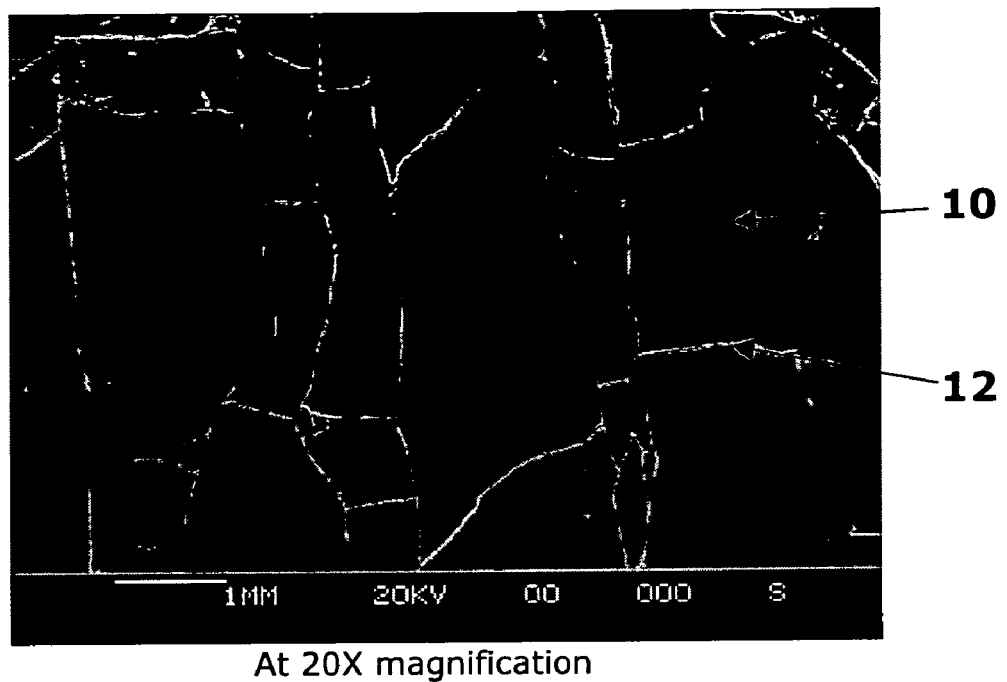
At 20X magnification
Fig. 6-a
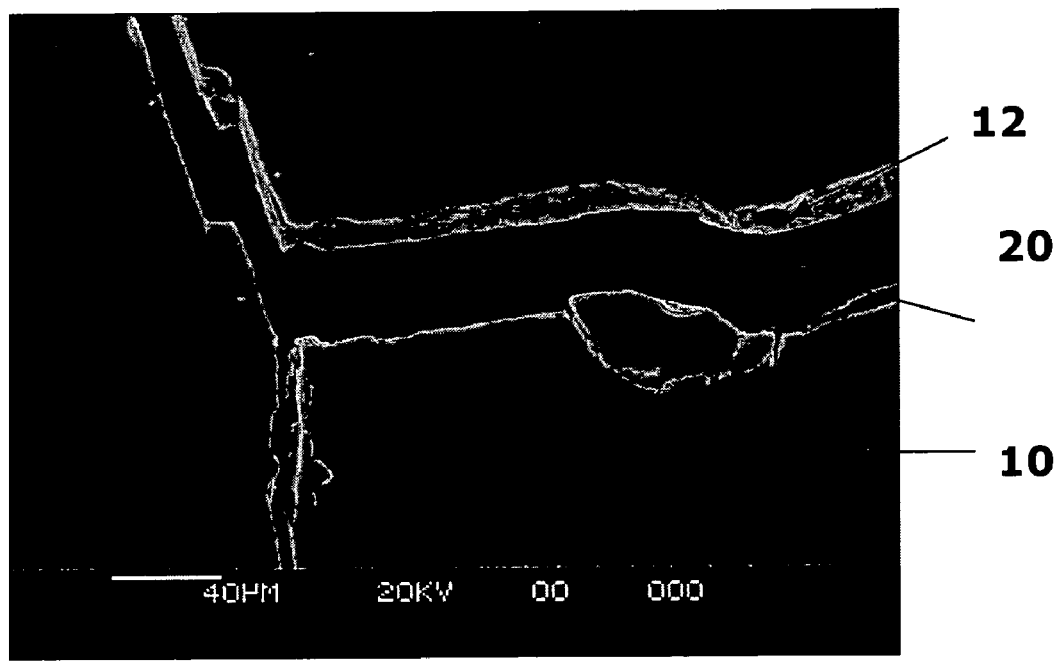
At 500X magnification
Fig. 6-b

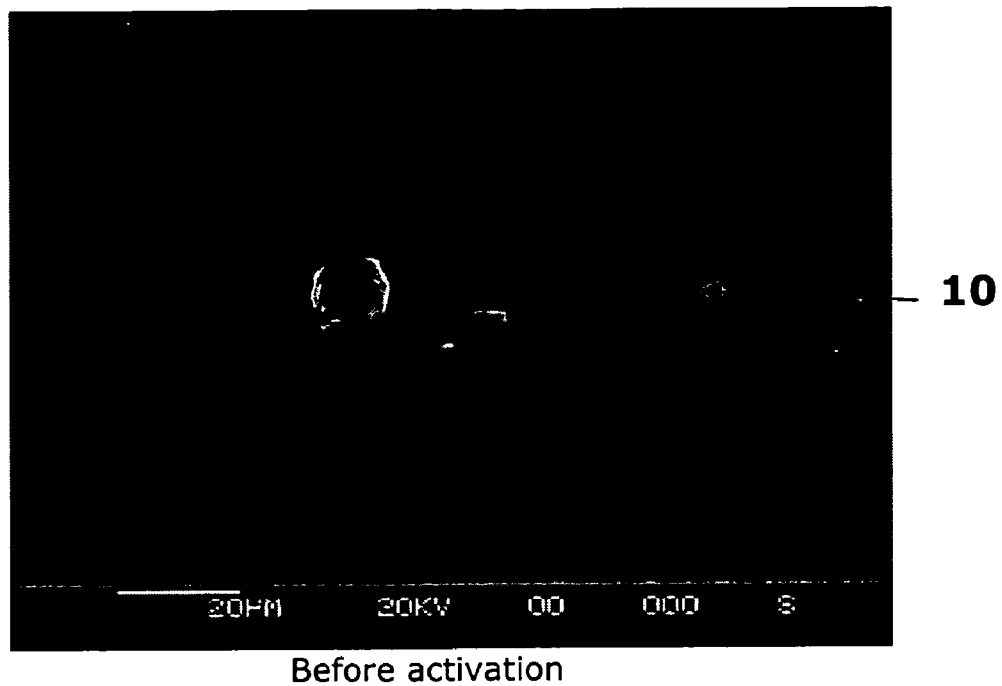
Before activation
Fig. 7-a
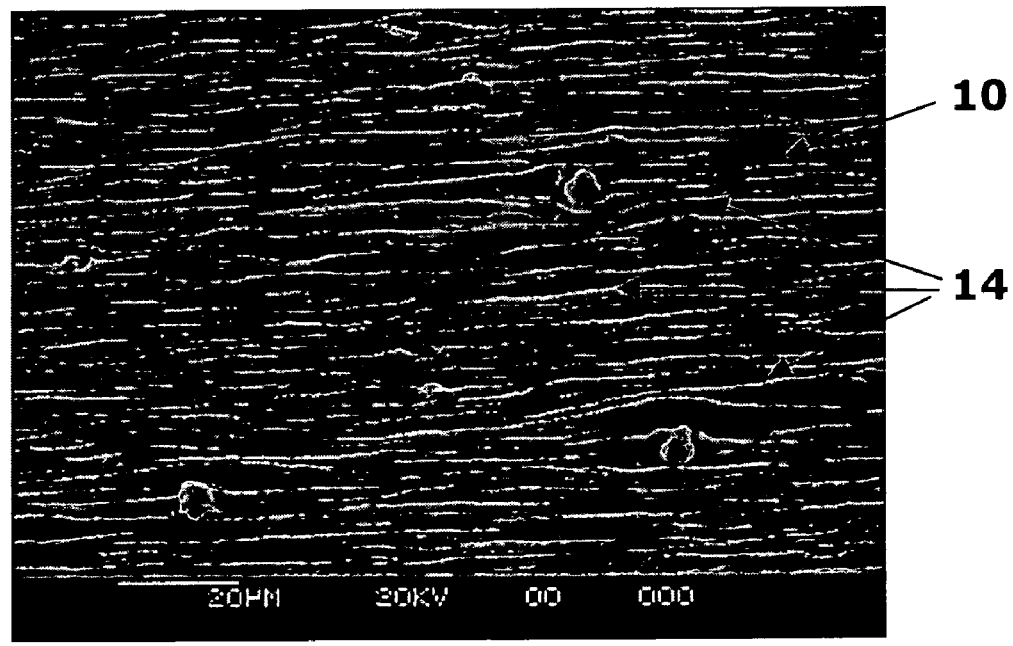
After activation
Fig. 7-b

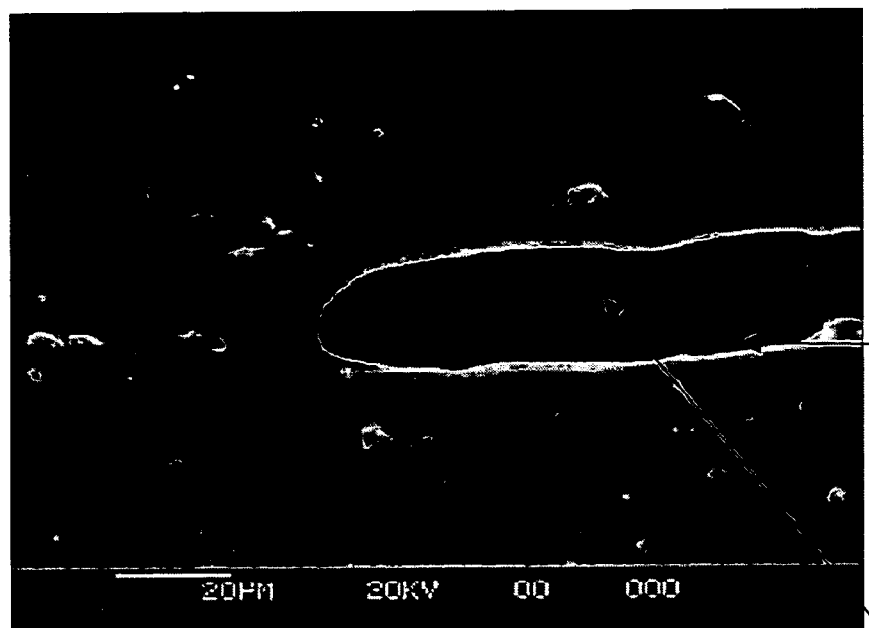
Before activation
Fig. 8-a
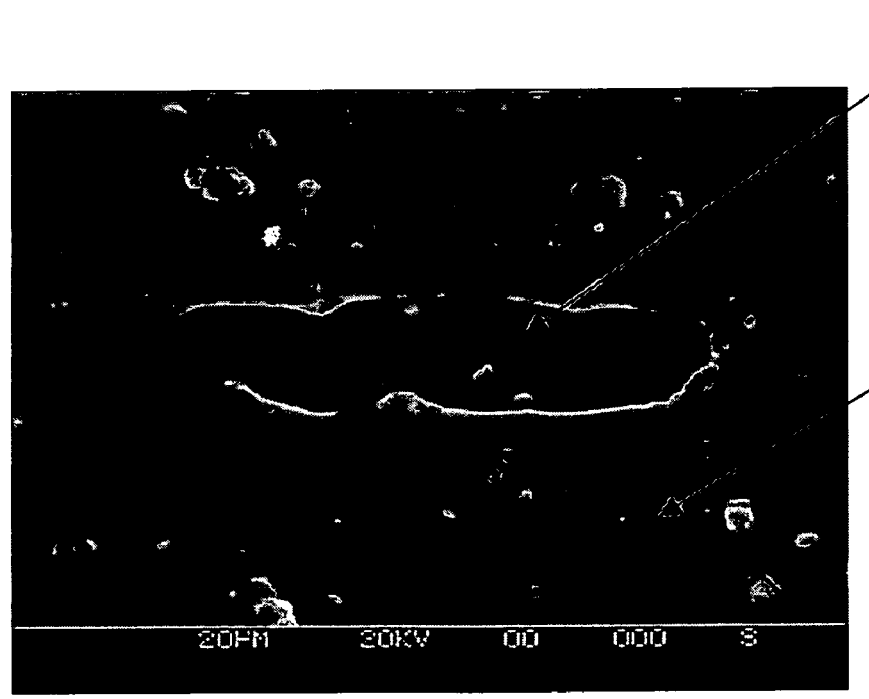
After activation
Fig. 8-b

US 7,879,452 B2

ELASTOMERIC FILMS WITH BRITTLE NONBLOCKING SKINS

RELATED APPLICATION

This application claims priority under 35 U.S.C. §119 of U.S. Application No. 60/680,168 filed May 12, 2005.

FIELD OF THE INVENTION

The present invention relates to nonblocking multilayer elastomeric films, and relates to methods of making nonblocking multilayer elastomeric films.

BACKGROUND OF THE INVENTION

Elastomeric materials have long been prized for their ability to expand to fit over or around a larger object, and then retract to provide a snug fit around the object. This quality has been prized for centuries, and much of Europe's early exploration was in search of rubber trees for their latex.

In recent years, synthetic polymeric elastomeric materials have supplemented or replaced natural rubber. Compounds such as polyurethane rubbers, styrene block copolymers, ethylene propylene rubbers, and other synthetic polymeric elastomers are well known in the art.

Elastomeric materials can take a variety of shapes. Elastomers can be formed as threads, cords, tapes, films, fabrics, and other diverse forms. The shape and structure of the elastomeric material is guided by the intended end use of the product. For instance, elastomers are often used in garments to provide a snug fit, such as in active wear. Elastomers can also form resilient but effective barriers, such as in the cuffs of thermal garments intended to retain body heat. In these applications, the elastomer is most often in the form of threads or filaments that are incorporated into the fabric of the garment. One example of a type of garment where both fit and barrier properties are important is hygienic products such as diapers. Elastomeric materials are used in the waist, around the leg openings, and in the fasteners (for a diaper) or sides (for an underpants-type garment). The elastomeric materials in these regions improve the overall fit of the garment, and also make it much easier to both don and remove the garment. The elastomeric materials also act as resilient barriers, improving the containment capabilities of the garment while still allowing comfort and free movement to the wearer.

In a hygienic product, the elastomer can be in the form of threads, fabrics, or films. Using elastomeric threads can pose challenges in assembling the garment, since the threads must be applied as one component of many in the manufacturing process. These threads can also be weak and they tend to break, which could lead to the elastic failing even if there are redundant threads present. Elastomeric fabrics are somewhat easier to work with in a manufacturing process, but the fabrics themselves tend to be expensive both in raw materials and in the cost of manufacturing the fabric itself. Elastomeric films are easier to use in manufacturing than threads and are less expensive than elastomeric fabrics to produce. Elastomeric films also tend to be stronger than threads or fabrics, and less likely to fail in use.

However, a disadvantage of elastomeric films is that the polymers used to make the films are inherently sticky or tacky. When elastomeric films are extruded and wound into a roll, the film will tend to stick to itself or "block," thereby becoming difficult or impossible to unwind. Blocking becomes more pronounced as the film is aged or stored in a warm environment, such as inside a storage warehouse.

The elastomeric blocking problem has been tackled in a number of ways. Antiblocking agents, which are usually powdered inorganic materials such as silica or talc, can be incorporated within the film. Antiblocking agents can also be dusted onto the outer surfaces of extruded film as the film is being formed. However, antiblocking agents must be added in large quantities to reduce blocking to an acceptable level, and these high levels of antiblock are detrimental to the elastomeric properties of the film. Another means of reducing blocking is to roughen the surface of the film, such as by embossing the film, which reduces the surface-to-surface contact of the rolled film and introduces minute air pockets that help reduce the blocking. Unfortunately, this also tends to create thinner, weaker areas of the film, which are then subject to tearing and failure when the film is stretched. Another means of reducing blocking is to incorporate a physical barrier, such as a release liner, into the roll between the layers of wound film. The release liner is then removed when the roll of film is unwound for further processing. The release liner is usually discarded, though, creating waste and a significant extra expense for the manufacturer. Yet another means of reducing elastomeric film blocking is by coextruding very thin outer layers, also called 'skins' or 'capping layers,' of an extensible or less elastomeric nonblocking polymer onto the surface of the elastomeric film. Suitable nonblocking polymers for these skins include polyolefins such as polyethylene or polypropylene. Such polyolefin skins are extensible but not elastomeric materials. They have little effect on the elastomeric properties of the film as a whole because they make up only a small fraction of the total composition of the film. However, these polyolefin skins will stretch and become irreversibly deformed when the elastomeric film as a whole is stretched or "activated" for the first time. When the stretching force on the activated elastomeric film is released, the elastomeric core will retract as it normally would. The stretched skins, which are not elastomeric, will instead wrinkle as the core retracts and create a microtextured surface.

There remains a need to effectively manufacture an elastomeric film that can be rolled and stored without blocking. Such a film should not have inferior elastomeric properties, should not create undue waste and manufacturing expense, and should present an appealing surface texture after activation.

SUMMARY OF THE INVENTION

In one embodiment, the present invention is directed to a nonblocking multilayer film. The nonblocking multilayer film comprises a first brittle polymer film layer and a second elastomeric polymer film layer, wherein the first polymer layer is bonded to the first surface of the second polymer film layer. The nonblocking multilayer film is activatable to fracture the first brittle polymer layer and to render the multilayer film elastomeric.

In another embodiment, the present invention is directed to a nonblocking multilayer elastomeric film. The nonblocking multilayer elastomeric film comprises a first brittle polymer film layer and a second elastomeric polymer film layer, wherein the first polymer layer is bonded to the first surface of the second polymer film layer. The multilayer film is activated to fracture the first brittle polymer film layer and to render the multilayer film elastomeric.

In another embodiment, the present invention is directed to a method of forming a nonblocking multilayer elastomeric film. The method comprises bonding a first brittle polymer film layer onto a first surface of a second elastomeric polymer film layer, to form a multilayer film. The multilayer film is then activated to fracture the first brittle polymer film layer and to render the multilayer film elastomeric.

In yet another embodiment, the present invention is directed to a method of forming a nonblocking multilayer elastomeric film. The method comprises providing a nonblocking multilayer film layer comprising a first brittle polymer film layer bonded to the first surface of a second elastomeric polymer film layer. The nonblocking multilayer film is then activated to fracture the brittle polymer film layer and to render the nonblocking multilayer film elastomeric.

Additional embodiments of the invention will be apparent in view of the following detailed description of the invention.

BRIEF DESCRIPTION OF THE DRAWINGS

The invention will be more fully understood in view of the drawings, in which:

FIGS. 1-a-1-d illustrate several possible structures for the inventive multilayer elastomeric film;

FIGS. 6-a and 6-b illustrate photomicrographs of an activated film of the present invention;

FIGS. 7-a and 7-b illustrate photomicrographs of comparative unactivated and activated films with extensible polyolefin skins; and FIGS. 8-a and 8-b illustrate photomicrographs of comparative unactivated and activated films with containing antiblock agents.

DETAILED DESCRIPTION OF THE INVENTION

Figure 2:
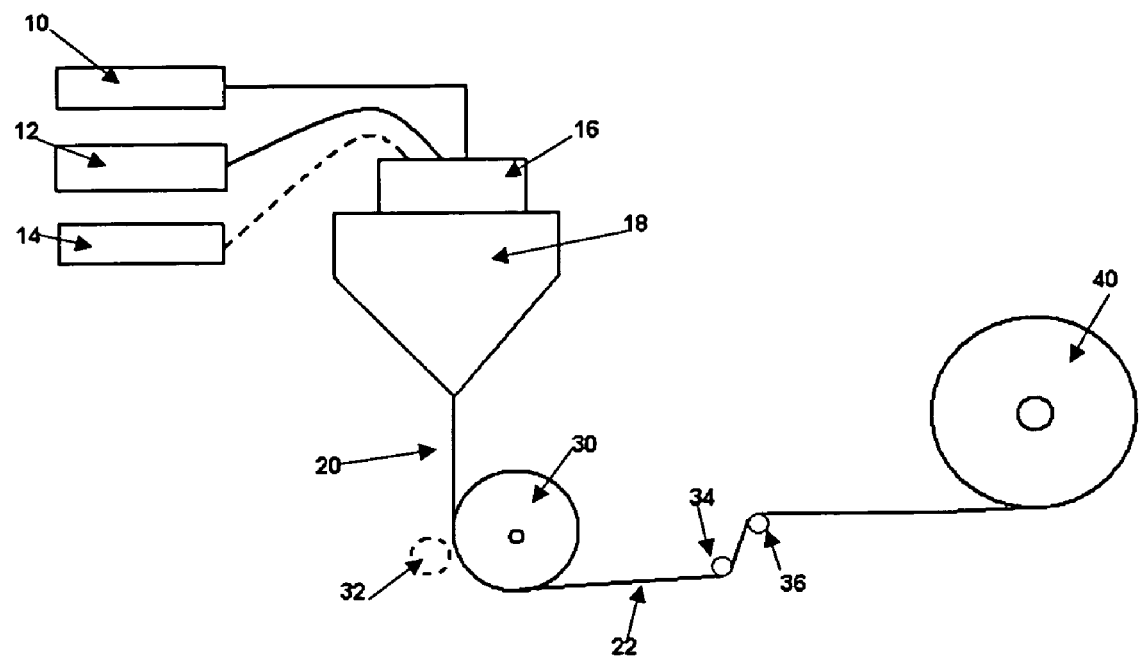
FIG. 2 is a schematic of a typical cast extrusion process.

The inventors have discovered that using a brittle nonblocking polymer as a layer bonded to the surface of an elastomeric film layer, instead of an extensible polymer skin, can dramatically reduce or eliminate the blocking experienced by an elastomeric film. The use of one or more brittle polymer film layers eliminates the need for extensible polyolefinic skins and creates no microtexture on the surface of the film. Unexpectedly, these multilayer films can be readily activated by known means, which fractures the brittle polymer film layer and renders the multilayer film elastomeric. Also unexpectedly, one or more brittle polymer film layers can be used as layers on the elastomeric film without reducing the elastomeric properties of the nonblocking multilayer elastomeric film significantly. Also unexpectedly, the brittle polymer film layer, whether it is unfractured or fractured, improves the tear strength of the nonblocking multilayer elastomeric film. The nonblocking multilayer elastomeric film can be wound into a roll, either before or after it is activated, and stored at normal room temperature for extended periods without significant blocking.

For the purpose of this disclosure, the following terms are defined:

"Film" refers to material in a sheet-like form where the dimensions of the material in the x (length) and y (width) directions are substantially larger than the dimension in the z (thickness) direction. Films have a z-direction thickness in the range of about 1 µm to about 1 mm.

"Laminate" as a noun refers to a layered structure of sheet-like materials stacked and bonded so that the layers are substantially coextensive across the width of the narrowest sheet of material. The layers may comprise films, fabrics, or other materials in sheet form, or combinations thereof. For instance, a laminate may be a structure comprising a layer of film and a layer of fabric bonded together across their width such that the two layers remain bonded as a single sheet under normal use. A laminate may also be called a composite or a coated material. "Laminate" as a verb refers to the process by which such a layered structure is formed.

"Coextrusion" refers to a process of making multilayer polymer films. When a multilayer polymer film is made by a coextrusion process, each polymer or polymer blend comprising a layer of the film is melted by itself. The molten polymers may be layered inside the extrusion die, and the layers of molten polymer films are extruded from the die essentially simultaneously. In coextruded polymer films, the individual layers of the film are bonded together but remain essentially unmixed and distinct as layers within the film. This is contrasted with blended multicomponent films, where the polymer components are mixed to make an essentially homogeneous blend or heterogeneous mixture of polymers that are extruded in a single layer.

"Extrusion lamination" or "extrusion coating" refer to processes by which a film of molten polymer is extruded onto a solid substrate, in order to coat the substrate with the polymer film and to bond the substrate and film together.

"Stretchable" and "recoverable" are descriptive terms used to describe the elastomeric properties of a material. "Stretchable" means that the material can be extended by a pulling force to a specified dimension significantly greater than its initial dimension without breaking. For example, a material that is 10 cm long that can be extended to about 13 cm long without breaking under a pulling force could be described as stretchable. "Recoverable" means that a material which is extended by a pulling force to a certain dimension significantly greater than its initial dimension without breaking will return to its initial dimension or a specified dimension that is adequately close to the initial dimension when the pulling force is released. For example, a material that is 10 cm long that can be extended to about 13 cm long without breaking under a pulling force, and which returns to about 10 cm long or to a specified length that is adequately close to 10 cm could be described as recoverable.

"Elastomeric" or "elastomer" refer to polymer materials which can be stretched to at least about 150% of their original dimension, and which then recover to no more than 120% of their original dimension, in the direction of the applied stretching force. For example, an elastomeric film that is 10 cm long should stretch to at least about 15 cm under a stretching force, then retract to no more than about 12 cm when the stretching force is removed. Elastomeric materials are both stretchable and recoverable.

"Extensible" refers to polymer materials that can be stretched at least about 130% of their original dimension without breaking, but which either do not recover significantly or recover to greater than about 120% of their original dimension and therefore are not elastomeric as defined above. For example, an extensible film that is 10 cm long should stretch to at least about 13 cm under a stretching force, then either remain about 13 cm long or recover to a length more than about 12 cm when the stretching force is removed. Extensible materials are stretchable, but not recoverable.

"Brittle" refers to polymeric materials that are highly resistant to stretching and cannot be stretched more than 110% of their original dimension without breaking or cracking. For example, a brittle film that is 10 cm long cannot be stretched to more than about 11 cm under a stretching force without fracturing. Brittle films do not recover or recover only minimally when the stretching force is removed. Brittle materials are neither stretchable nor recoverable.

"Blocking" refers to the phenomenon of a film sticking to itself while rolled, folded, or otherwise placed in intimate surface-to-surface contact, due to the inherent stickiness or tackiness of one or more of the film components. Blocking can be quantified by ASTM D3354 "Blocking Load of Plastic Film by the Parallel Plate Method."

"Nonblocking" refers to a material that does not block when placed in intimate contact with itself.

"Skin" or "skins" refer to thin outer layers of polymer film on one or both sides of another, central core of polymer film. For example, in the case of an ABA film structure, the A layers would be the skins.

"Core layer" or "core layers" refers to an inner layer or layers of polymer film that are not the skins. For example, in an ABA film structure, the B layer is the core. In an ABCBA film structure, the B and C layers are all core layers.

"Activation" or "activating" refers to a process by which the elastomeric film or material is rendered easy to stretch. Most often, activation is a physical treatment, modification or deformation of the elastomeric film. Stretching a film for the first time is one means of activating the film. An elastomeric material that has undergone activation is called "activated." A common example of activation is blowing up a balloon. The first time the balloon is inflated (or "activated"), the material in the balloon is stretched. If the balloon is difficult to blow up, the person inflating the balloon will often manually stretch the uninflated balloon to make the inflation easier. If the inflated balloon is allowed to deflate and then blown up again, the "activated" balloon is much easier to inflate.

"Film strength" or "mechanical strength" are the tensile properties of a film, as measured by ASTM D-822 "Tensile Properties of Thin Plastic Sheeting". Unless noted otherwise, "film strength" or "mechanical strength" refers specifically to tensile at break and % elongation at break.

"Tear strength" is a property of a film which determines the ease or difficulty by which the film can be torn starting from a notch or aperture cut into the film. The brittle polymers used in the first polymer film layer, or "skin" layer, of the films and methods of this invention may comprise any common extrudable, brittle polymer that can be formed into a film as known in the art, such as polystyrene, polymethylmethacrylate, other acrylate polymers, polyesters, polycarbonates, etc. Without wishing to be bound by theory, the inventors believe that a polymer with a high degree of crystallinity is required to display the required brittleness. One brittle polymer that is particularly preferred is highly crystalline polystyrene. For example, suitable polystyrene resins can be obtained from The Dow Chemical Company of Midland, Mich. or NOVA Chemicals Corporation of Calgary, Alberta, among others.

Another layer of brittle polymer film may be used as a second skin layer for the films and methods of this invention. If there are two brittle polymer film skin layers one the elastomeric polymer film layer in the core of the inventive film, the skin layers may comprise the same composition (e.g. an ABA film) or different compositions (e.g. an ABC film) comprising a brittle polymer. For nonblocking multilayer elastomeric films comprising a single skin layer or two skin layers, each skin layer of the nonblocking multilayer elastomeric film should comprise from about 0.5% to 20% of the total weight of the multilayer film, and hence the core layer(s) should comprise about 60% to 99% of the total weight of the multilayer film.

The elastomeric polymers used in the second polymer film layer of the films and methods of this invention may comprise any extrudable elastomeric polymer. Examples of such elastomeric polymers include block copolymers of vinyl arylene and conjugated diene monomers, natural rubbers, polyurethane rubbers, polyester rubbers, elastomeric polyolefins and polyolefin blends, elastomeric polyamides, or the like. The elastomeric film may also comprise a blend of two or more elastomeric polymers of the types previously described. Preferred elastomeric polymers are the block copolymers of vinyl arylene and conjugated diene monomers, such as AB, ABA, ABC, or ABCA block copolymers where the A segments comprise arylenes such as polystyrene and the B and C segments comprise dienes such as butadiene, isoprene, or ethylene butadiene. Suitable block copolymer resins are readily available from KRATON Polymers of Houston, Tex. or Dexco Polymers LP of Planquemine, La.

The nonblocking multilayer elastomeric film of the present invention may include other components to modify the film properties, aid in the processing of the film, or modify the appearance of the film. These additional components may be the same or may vary for each layer present. For example, polymers such as polystyrene homopolymer or high-impact polystyrene may be blended with the elastomeric polymer in the core layer of the film in order to stiffen the film and improve the strength properties. Viscosity-reducing polymers and plasticizers may be added as processing aids. Other additives such as pigments, dyes, antioxidants, antistatic agents, slip agents, foaming agents, heat and/or light stabilizers, and inorganic and/or organic fillers may be added. Each additive may be present in one, more than one, or all of the layers of the multilayer film.

FIGS. 1-a-1-d show several possible embodiments of the nonblocking multilayer elastomeric films of the present invention. In each of FIGS. 1-a-1-d: 10 represents an A layer, which may be a brittle polymeric film layer; 20 represents a B layer, which may be an elastomeric polymeric film layer; and 30 represents a C layer, which may be a brittle polymeric film layer if it is a skin layer or an elastomeric polymeric film layer if it's a skin or core layer. Hence, FIG. 1-a represents an AB film structure, FIG. i-b represents an ABA film structure, FIG. 1-c represents an ABC film structure and FIG. 1-d represents an ABCBA film structure. Additional embodiments and combinations of film layers will be understood by one skilled in the art as within the scope of the present invention.

Any film-forming process can prepare the inventive nonblocking multilayer elastomeric film. In a specific embodiment, a coextrusion process, such as cast coextrusion or blown-film coextrusion, is used to form the nonblocking multilayer elastomeric film. Coextrusion of multilayer films by cast or blown processes are well known.

FIG. 2 illustrates a schematic for a typical cast coextrusion film process. The film in this example could be an AB, ABA, ABC, ABCBA, or other such multilayer film comprising two or more distinct polymeric compositions. One elastomeric polymer composition is melted in a conventional screw extruder 10. Extruder 12 is used to melt another polymeric composition. Additional extruders 14 etc. may be added, particularly if three or more polymeric compositions are required. The molten polymer compositions are then transferred from the extruders to the feed block 16 that aligns the individual compositions for coextrusion into a multilayer film. The molten polymer is then extruded into a web 20 from the extrusion die 18. The molten polymer web 20 is cast onto a chill roll 30 where the web is rapidly cooled to form the film 22. The chill roll 30 may be a smooth roll that makes a smooth film, or an embossing roll which embosses a pattern onto the surface of the film. An optional backing roll 32 can assist the chill roll 30 in forming the film 22. The film 22 may then pass over optional equipment such as idler rolls 34 and 36, that facilitate the transfer of the film from the cast extrusion section to winder 40 where it is wound and stored to await further processing.

Figure 3:
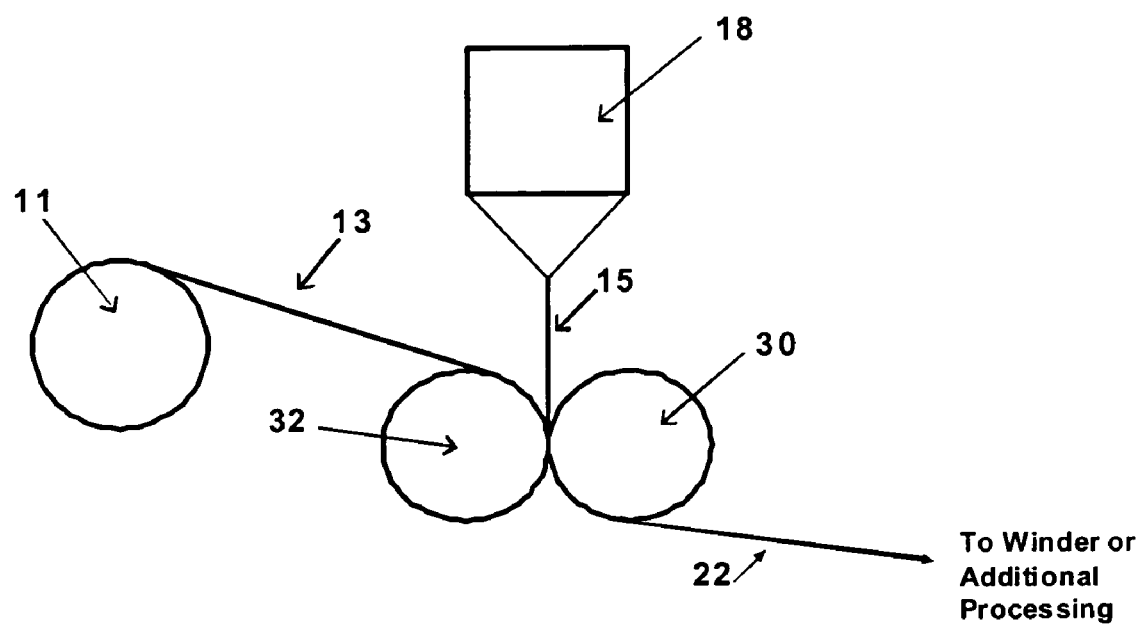
FIG. 3 is a schematic of a typical extrusion coating process.

In another embodiment, an extrusion coating process is used to form the nonblocking multilayer elastomeric film. Such extrusion coating processes are well known. FIG. 3 illustrates a typical extrusion coating process. A polymeric film layer 15 is melt-extruded through a film-forming die 18 and drops to the nip between the illustrated metal roll 30 and rubber roll 32. The metal roll may be chilled to rapidly cool the molten polymer film. The metal roll 30 may also be engraved with an embossing pattern if such a pattern is desired on the resulting film. The other polymer film layer of the nonblocking multilayer film 13 is unwound from roll 11 and introduced into the nip between the metal and rubber rolls as well. Note that the extruded film layer 15 may be either the brittle polymer film layer or the elastomeric polymer film layer of the present invention; conversely, the other polymer film layer 13 will be the other polymeric film layer of the present invention. The extruded film layer 15 and other film layer 13 are pressed together at the nip to bond the layers. The nonblocking multilayer film 22 may now be wound into a roll or go on for further processing.

Figure 4:
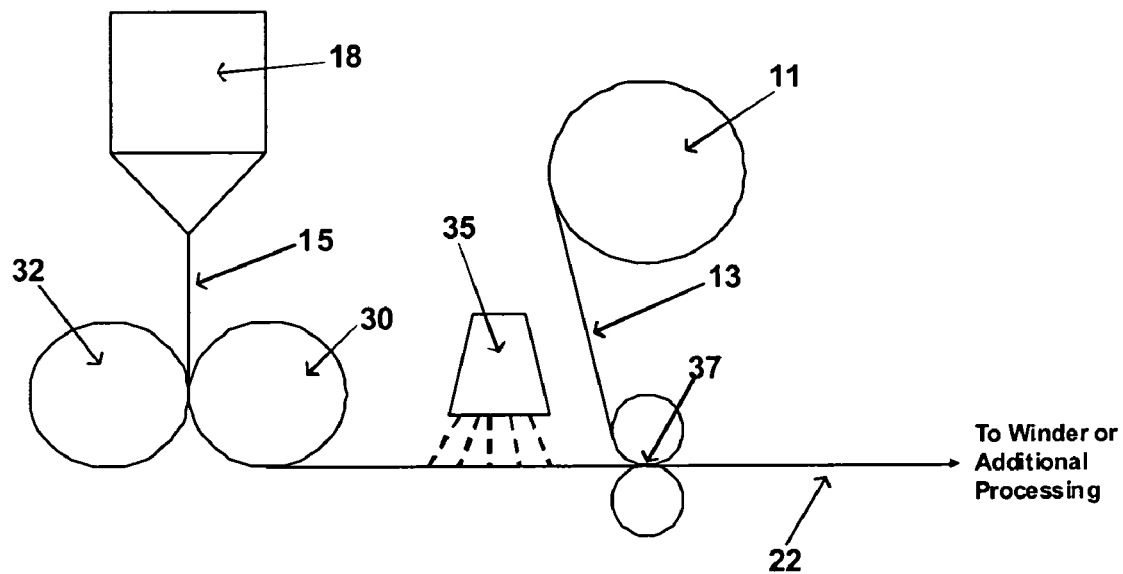
FIG. 4 is a schematic of a typical adhesive lamination process.

Another embodiment of a method to form the inventive nonblocking multilayer elastomeric film is adhesive lamination, illustrated in FIG. 4. One polymeric film layer 15 is melt-extruded from a film-forming die 18 and drops to the nip between the illustrated metal roll 30 and rubber roll 32. The metal roll 30 may be chilled to rapidly cool the molten polymer film. The metal roll may also be engraved with an embossing pattern if such a pattern is desired on the resulting film. After the extruded film layer has cooled and solidified, it passes to an adhesive bonding station, where adhesive is applied by means such as a spray unit 35 onto the film. Alternatively, the spray unit 35 may spray adhesive onto the incoming polymeric film layer 13. The other polymer film layer of the nonblocking multilayer film 13 from roll 11 is introduced into a nip 37 that presses the extruded film layer 15 and the other film layer 13 to bond the layers. Note that the extruded film layer 15 may be either the brittle polymer film layer or the elastomeric polymer film layer of the present invention; conversely, the other polymer film layer 13 will be the other polymeric film layer of the present invention. The nonblocking multilayer film 22 may now be wound into a roll or go on for further processing.

Other known bonding methods may be used to bond the polymer film layers of the inventive nonblocking multilayer film. Such methods include thermal bonding, ultrasonic bonding, calender bonding, point bonding, and laser bonding. Combinations of bonding methods are also within the scope of the present invention.

In order to render the inventive nonblocking multilayer film elastomeric, it is necessary to activate the film. The brittle polymer film layer on the nonblocking multilayer film must be broken, fractured or cracked, so that the skin becomes discontinuous and the elastomer in the core layer is capable of stretching under the cracked portions of the skin. The inventive film can be activated in a number of ways. For instance, the film can be stretched, folded, scored, corrugated, embossed, calendered with a patterned roll, or otherwise deformed in such a way that the skin layer is broken. A preferred means of stretching the film is by known stretching techniques, such as machine-direction orientation (MDO), tentering, or incremental stretching. A particularly preferred method of activating the film is by incrementally stretching the film between intermeshing rollers, as described in U.S. Pat. No. 4,144,008. Incremental stretching has the advantage that the skin can be preferentially broken in only the cross direction (CD), in order to make the film stretchable in only the CD direction, or in only the machine direction (MD), in order to make the film stretchable in only the MD directions. The film may also be activated in both CD and MD, in order to make the material stretchable in both directions.

It has been found unexpectedly that the brittle polymer film layer on the elastomeric polymer film layer will prevent the nonblocking multilayer elastomeric film from blocking if it is wound and stored for a period of time at normal storage temperatures. This is true whether the nonblocking multilayer elastomeric film is stored in an activated or unactivated state. It is to be understood that additional processing steps such as aperturing the nonblocking multilayer elastomeric film, printing the film, slitting the film, laminating additional layers to the film, and other such processes may be added and are within the scope of this invention.

The inventive film may be laminated to a substrate layer by known lamination means. The substrate layer can be any extensible sheet-like material, such as another polymer film, a fabric, or paper. In one nonlimiting embodiment, the substrate layer is a nonwoven web. Examples of suitable nonwoven webs include spunbond, carded, meltblown, and spunlaced nonwoven webs. These webs may comprise fibers of polyolefins such as polypropylene or polyethylene, polyesters, polyamides, polyurethanes, elastomers, rayon, cellulose, copolymers thereof, or blends thereof or mixtures thereof. Paper products, such as tissue or tissue-like products comprising cellulose-based or cellulosic fibers formed into a mat, are considered nonwoven fibrous webs or nonwoven materials that fall within the scope of this invention. The nonwoven webs may also comprise fibers that are homogenous structures or comprise bicomponent structures such as sheath/core, side-by-side, islands-in-the-sea, and other known bicomponent configurations. For a detailed description of nonwovens, see "Nonwoven Fabric Primer and Reference Sampler" by E. A. Vaughn, Association of the Nonwoven Fabrics Industry, 3d Edition (1992). Such nonwoven fibrous webs typically have a weight of about 5 grams per square meter (gsm) to 75 gsm. For the purpose of the present invention, the nonwoven may be very light, with a basis weight of about 5 to 20 gsm or any other basis weight which is adequate to prevent roll blocking when laminated to the desired elastomeric film. However, a heavier nonwoven, with a basis weight of about 20 to 75 gsm, may be desired in order to achieve certain properties, such as a pleasant cloth-like texture, in the resulting laminate or end-use product.

Also, within the scope of this invention are other types of substrate layers, such as woven fabrics, knitted fabrics, scrims, netting, etc. These materials may certainly be used as the protective layer that prevents the elastomeric film layer from roll blocking. However, because of cost, availability, and ease of processing, nonwoven fabrics are usually preferred for the laminates in the inventive process.

The inventive film may be laminated to the substrate layer by known lamination means. These lamination means include extrusion lamination, adhesive lamination, thermal bonding, ultrasonic bonding, calender bonding, point bonding, and laser bonding, and other such means. Combinations of these bonding methods are also within the scope of the present invention.

The inventive nonblocking multilayer elastomeric film may also be laminated to two or more such substrate layers, as described above.

The inventive nonblocking multilayer elastomeric film can be laminated to one or more substrate layers at any point in the process. Specifically, the film can be laminated to a substrate layer before or after the film is activated. In the case of most non-elastomeric substrate layers, it is desirable to either perform the lamination prior to activation and then activate the laminate. Alternatively, the nonblocking multilayer elastomeric film may be activated, the substrate layer may be laminated to the activated nonblocking multilayer elastomeric film, then the laminate is activated a second time to allow all layers of the laminate to stretch easily. If the activated film is to be laminated to a non-elastomeric substrate and post-lamination activation is not desirable, the non-elastomeric substrate can be necked, ruffled, crinkled, folded, gathered, or otherwise treated to allow the film component of the laminate to stretch without tearing or damaging the second substrate.

The following examples are presented to illustrate diverse aspects of the present invention. These examples are not intended to limit the invention in any way.

Example 1

Figure 5:
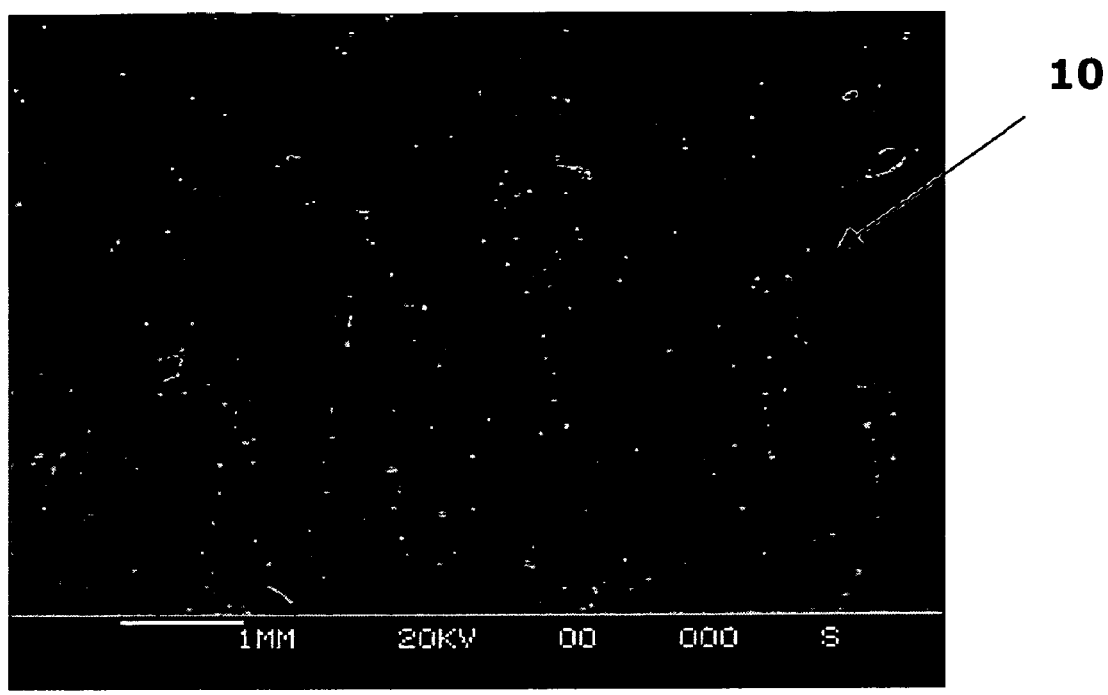
FIG. 5 illustrates photomicrographs of an unactivated film of the present invention.

An elastomeric film was formed by a cast-extrusion process. The film comprised a multilayer ABA construction, where the A layers were on the surface and the B layer was in the core. The A layers comprised a crystalline polystyrene (NOVA® 3900 from NOVA Chemicals®). The B layer comprised a styrene-butadiene-styrene (SBS) block copolymer (Vector™ 7400 from Dexco™ Polymers LP). The A and B layers were coextruded into a film where each of the A layers were about 20 µm thick and the B layer was about 80 µm thick. This film was wound without further processing. FIG. 5 shows an SEM photomicrograph of the film of Example 1 in plane view. The A (brittle polymer film) layer 10 is visible in this photomicrograph.

Example 2

The elastomeric film of Example 1 was activated by incremental stretching in both the CD and MD directions. The CD and MD incremental stretching methods employed were as described in U.S. Pat. No. 5,865,926. The activated film could be easily stretched manually in both the CD and MD directions. FIGS. 6-a and 6-b illustrate SEM photomicrographs of the incrementally stretched film of Example 2. The surface cracking 12 of the polystyrene skin 10 on the elastomeric film layer 20 can be clearly seen in these FIGS. This contrasts sharply with the smooth surface seen in FIG. 5. Indeed, the surface cracks in the film of FIGS. 6-a and 6-b have sharp boundaries, and the core layer of elastomer 20 can be seen in the gaps between the cracks 12.

COMPARATIVE EXAMPLE 1

An elastomeric film was formed by a cast-extrusion process. The film comprised a multilayer ABA construction, where the A layers were on the surface and the B layer was in the core. The A layers comprised about 80% LLDPE (Attane® 4202 from the Dow Chemical Company) and about 20% LDPE (Dow® LDPE 640 from the Dow Chemical Company). The B layer comprised about 58% styrene-isoprene-styrene (SIS) block copolymer (Vector™ 4111 from Dexco Polymers LP), 19% styrene-butadiene-styrene (SBS) block copolymer (Vector™ 8508 from Dexco Polymers LP), 19% LDPE (Affinity® EG 8200 from Dow Chemical Company), and 4% white masterbatch concentrate (Ampacet® 7188763 from Ampacet Corporation). The A and B layers were coextruded into a film where the A layers were about 4 µm thick and the B layer was about 65 µm thick. This film was wound without being processed after being formed.

A portion of the film of Comparative Example 1 was activated by stretching the film in the CD direction. The activated film could then be easily stretched manually in the CD direction. FIGS. 7-a and 7-b illustrate SEM photomicrographs of both the unactivated and activated film of Comparative Example 1. In this case, the unactivated film skin layer 10 has a smooth surface, but the activated film skin layer 10 clearly shows wrinkling and microtexturing 14 of the extensible polyethylene skins. The skins, although textured, are still continuous across the surface of the film. The appearance of this film is quite different from the activated film of Example 2, where the surface cracking of the polystyrene skins on the elastomeric film can be clearly seen in FIGS. 6-a and 6-b. Note that in both films, particles of the white masterbatch colorant can be seen.

COMPARATIVE EXAMPLE 2

An elastomeric film was formed by a cast-extrusion process. The film comprised a multilayer ABA construction, where the A layers were on the surface and the B layer was in the core. The A layers comprised about 60% SIS block copolymer (Vector™ 4211A from Dexco™ Polymers LP) and about 40% antiblock masterbatch (AB MB 6017-PS from Polytechs SAS, comprising about 20% synthetic silica antiblock agent in a polystyrene carrier resin), which resulted in a final antiblock concentration of about 8% in each A layer. The B layer comprised about 46% SIS block copolymer (Vector™ 4211A from Dexco™ Polymers LP), 21% SBS block copolymer (Vector™ 7400 from Dexco™ Polymers LP), 30% antiblock masterbatch (AB MB 6017-PS from Polytechs SAS, comprising about 20% synthetic silica antiblock agent in a polystyrene carrier resin), which resulted in a final antiblock concentration of about 6% in each B layer, and 3% white masterbatch concentrate (Schulman® 8500 from Schulman Corporation). The A and B layers were coextruded into a film where each of the A layers were about 4 µm thick and the B layer was about 65 µm thick. This film was wound without further processing.

A portion of the film of Comparative Example 2 was activated by stretching the film in the CD direction. The activated film could then be easily stretched manually in the CD direction. The activated film could be easily stretched manually in both the CD and MD directions. FIGS. 8-a and 8-b illustrate SEM photomicrographs of both the unactivated and activated film of Comparative Example 2. The rupture 16 shown in the skin layer 10 occurred during the extrusion process. Except for this rupture, though, the unactivated and activated film have smooth surfaces, with no sign of either the cracking of Example 2 or the microtexturing of Comparative Example 1. Also, particles of the antiblock agent are visible in both photomicrographs.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A nonblocking multilayer film, comprising a first brittle polymer film layer which cannot be stretched more than 110% of its original dimension without breaking or cracking and a second elastomeric polymer film layer, wherein the brittle polymer is selected from the group consisting of polystyrene, acrylate polymers, polycarbonates, and combinations thereof and the first polymer layer is bonded to the first surface of the second polymer film layer, and wherein the multilayer film is activatable to fracture the first brittle polymer film layer and to render the multilayer film elastomeric, which can be stretched to at least about 150% of its original dimension, and which then recovers no more than 120% of its original dimension.

2. The nonblocking multilayer film of claim 1 wherein the first polymer film layer and the second polymer film layer are bonded by coextrusion.

3. The nonblocking multilayer film layer of claim 1 wherein the first polymer film layer and the second polymer film layer are bonded by extrusion coating.

4. The nonblocking multilayer film of claim 3 wherein the first polymer film layer is extrusion coated onto the second polymer film layer.

5. The nonblocking multilayer film of claim 3 wherein the second polymer film layer is extrusion coated onto the first polymer film layer.

6. The nonblocking multilayer film of claim 1 wherein the first polymer film layer and the second polymer film layer are bonded by a method selected from the group consisting of adhesive bonding, thermal bonding, ultrasonic bonding, calender bonding, point bonding, and combinations thereof.

7. The nonblocking multilayer film of claim 1, further comprising activating the multilayer film to fracture the first polymer film layer and to render the multilayer film elastomeric.

8. The nonblocking multilayer film of claim 7 wherein the multilayer film is activated by stretching.

9. The nonblocking multilayer film of claim 8 wherein the multilayer film is stretched by a method selected from the group consisting of incremental stretching, machine-direction orientation, tentering, and combinations thereof.

10. The nonblocking multilayer film of claim 1 wherein the second polymer film layer comprises an elastomeric polymer selected from the group consisting of block copolymers of vinyl arylene and conjugated diene monomers, natural rubbers, polyurethane rubbers, polyester rubbers, elastomeric polyolefins, elastomeric polyamides, and blends thereof.

11. The nonblocking multilayer film of claim 1 wherein the second polymer film layer comprises a blend of elastomeric polymers and high-impact polystyrene.

12. The nonblocking multilayer film of claim 1 wherein the second polymer film layer comprises a multilayer elastomeric film layer.

13. The nonblocking multilayer film of claim 1, further comprising bonding a third polymer film layer comprising a brittle polymer to the multilayer film on the second surface of the second polymer film layer.

14. The nonblocking multilayer film of claim 13 wherein the third polymer film layer and the multilayer film are bonded by a method selected from the group consisting of coextrusion, extrusion coating, adhesive bonding, thermal bonding, ultrasonic bonding, calender bonding, point bonding, and combinations thereof.

15. The nonblocking multilayer film of claim 1, further comprising bonding the multilayer film to a third substrate layer.

16. The nonblocking multilayer film of claim 15, wherein the third substrate layer comprises a polymer film layer, nonwoven fabric, paper product, woven fabric, knitted fabric, scrim, netting, or combination thereof.

17. The nonblocking multilayer elastomeric film of claim 15 wherein the third substrate layer and the multilayer film are bonded by a method selected from the group consisting of coextrusion, extrusion coating, adhesive bonding, thermal bonding, ultrasonic bonding, calender bonding, point bonding, and combinations thereof.

18. The nonblocking multilayer film of claim 15, further comprising bonding the multilayer film to a plurality of substrate layers, wherein the plurality of substrate layers comprise one or more substrates selected from the group consisting of a polymer film layer, nonwoven fabric, paper product, woven fabric, knitted fabric, scrim, netting, and combinations thereof.

19. The nonblocking multilayer film of claim 1, further comprising aperturing the nonblocking multilayer film.

20. A nonblocking multilayer elastomeric film, comprising a first brittle polymer film layer which cannot be stretched more than 110% of its original dimension without breaking or cracking and a second elastomeric polymer film layer, wherein the brittle polymer is selected from the group consisting of polystyrene, acrylate polymers, polycarbonates, and combinations thereof and the first polymer layer is bonded to the first surface of the second polymer film layer, and wherein the multilayer film is activated to fracture the first brittle polymer film layer and to render the multilayer film elastomeric, which can be stretched to at least about 150% of its original dimension, and which then recovers no more than 120% of its original dimension.

21. The nonblocking elastomeric multilayer film of claim 20 wherein the first polymer film layer and the second polymer film layer are bonded by coextrusion.

22. The nonblocking elastomeric multilayer film of claim 20 wherein the first polymer film layer and the second polymer film layer are bonded by extrusion coating.

23. The nonblocking elastomeric multilayer film of claim 22 wherein the first polymer film layer is extrusion coated onto the second polymer film layer.

24. The nonblocking elastomeric multilayer film of claim 22 wherein the second polymer film layer is extrusion coated onto the first polymer film layer.

25. The nonblocking elastomeric multilayer film of claim 22 wherein the first polymer film layer and the second polymer film layer are bonded by a method selected from the group consisting of adhesive bonding, thermal bonding, ultrasonic bonding, calender bonding, point bonding, and combinations thereof.

26. The nonblocking elastomeric multilayer film of claim 20 wherein the multilayer film is activated by stretching.

27. The nonblocking elastomeric multilayer film of claim 20 wherein the multilayer film is stretched by a method selected from the group consisting of incremental stretching, machine-direction orientation, tentering, and combinations thereof.

28. The nonblocking elastomeric multilayer film of claim 20 wherein the second polymer film layer comprises an elastomeric polymer selected from the group consisting of block copolymers of vinyl arylene and conjugated diene monomers, natural rubbers, polyurethane rubbers, polyester rubbers, elastomeric polyolefins, elastomeric polyamides, and blends thereof.

29. The nonblocking elastomeric multilayer film of claim 28 wherein the second polymer film layer comprises a blend of elastomeric polymers and high-impact polystyrene.

30. The nonblocking elastomeric multilayer film of claim 20 wherein the second polymer film layer comprises a multilayer elastomeric film.

31. The nonblocking elastomeric multilayer film of claim 20, further comprising bonding a third polymer film layer comprising a brittle polymer to the multilayer film on the second surface of the second polymer film.

32. The nonblocking elastomeric multilayer film of claim 31 wherein the third polymer film layer and the multilayer film are bonded by a method selected from the group consisting of coextrusion, extrusion coating, adhesive bonding, thermal bonding, ultrasonic bonding, calender bonding, point bonding, and combinations thereof.

33. The nonblocking elastomeric multilayer film of claim 20, further comprising bonding the multilayer film to a third substrate layer.

34. The nonblocking elastomeric multilayer film of claim 33, wherein the third substrate layer comprises a polymer film layer, nonwoven fabric, paper product, woven fabric, knitted fabric, scrim, netting, or combination thereof.

35. The nonblocking elastomeric multilayer elastomeric film of claim 33 wherein the third substrate layer and the multilayer film are bonded by a method selected from the group consisting of coextrusion, extrusion coating, adhesive bonding, thermal bonding, ultrasonic bonding, calender bonding, point bonding, and combinations thereof.

36. The nonblocking elastomeric multilayer film of claim 33, further comprising bonding the multilayer film to a plurality of substrate layers, wherein the plurality of substrate layers comprise one or more substrates selected from the group consisting of a polymer film layer, nonwoven fabric, paper product, woven fabric, knitted fabric, scrim, netting, and combinations thereof.

37. The nonblocking elastomeric multilayer film of claim 20, further comprising aperturing the nonblocking elastomeric multilayer film.

38. The nonblocking multilayer film of claim 1, wherein the first polymer film layer comprises polystyrene.

39. The nonblocking multilayer film of claim 20, wherein the first polymer film layer comprises polystyrene.

40. The nonblocking multilayer film of claim 15, wherein the third substrate layer comprises a nonwoven fabric, paper product, woven fabric, knitted fabric, scrim, netting, or combination thereof.

41. The nonblocking elastomeric multilayer film of claim 33, wherein the third substrate layer comprises a nonwoven fabric, paper product, woven fabric, knitted fabric, scrim, netting, or combination thereof.

* * * * *